United States Patent [19]
Koest

[11] Patent Number: 5,975,700
[45] Date of Patent: Nov. 2, 1999

[54] DEVICE FOR THE TOPOGRAPHICAL MEASUREMENT OF A SURFACE OF A HUMAN EYE

[75] Inventor: Gert Koest, Hanover, Germany

[73] Assignee: Oculus Optikgeraete GmbH, Wetzlar, Germany

[21] Appl. No.: 09/000,436

[22] PCT Filed: Sep. 27, 1996

[86] PCT No.: PCT/EP96/04269

§ 371 Date: Jan. 30, 1998

§ 102(e) Date: Jan. 30, 1998

[87] PCT Pub. No.: WO97/14351

PCT Pub. Date: Apr. 24, 1997

[30] Foreign Application Priority Data

Oct. 17, 1995 [DE] Germany .......................... 195 38 567

[51] Int. Cl.[6] .................................................. A61B 3/10
[52] U.S. Cl. .......................................... 351/221; 351/212
[58] Field of Search ................................ 351/212, 221, 351/247

[56] References Cited

U.S. PATENT DOCUMENTS 5,500,697  3/1996  Fujieda ..................................... 351/212
5,684,562  11/1997  Fujieda ..................................... 351/212

FOREIGN PATENT DOCUMENTS

| 0 397 962 | 11/1990 | European Pat. Off. . |
| 0 589 857 | 3/1994 | European Pat. Off. . |
| 26 41 004 | 3/1978 | Germany . |
| 32 33 178 C2 | 3/1984 | Germany . |
| 43 25 494 A1 | 7/1994 | Germany . |
| 2 246 874 | 2/1992 | United Kingdom . |

*Primary Examiner*—Huy Mai
*Attorney, Agent, or Firm*—Flynn, Thiel, Boutell & Tanis, P.C.

[57] ABSTRACT

A device for measuring a spherical surface, in particular the cornea of a human eye, can be made compact and not liable to cause heating when in use by the use as the requisite light sources for producing a pattern on the said surface of a system of light-emitting diodes whose emission is supported by a reflector behind a mask which forms the pattern. The device can also be used to determine the reaction of the pupil to glare, by reflecting an external light source into the beam path.

18 Claims, 3 Drawing Sheets

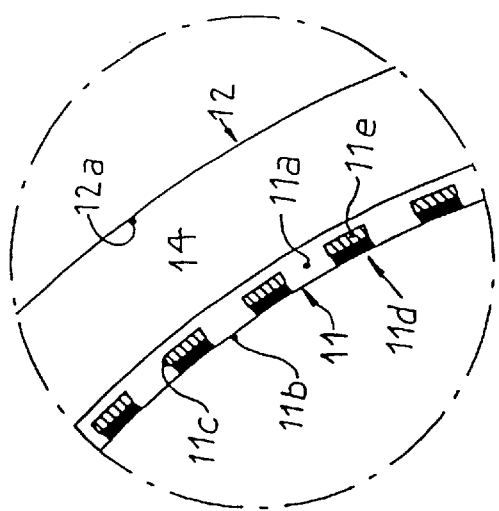
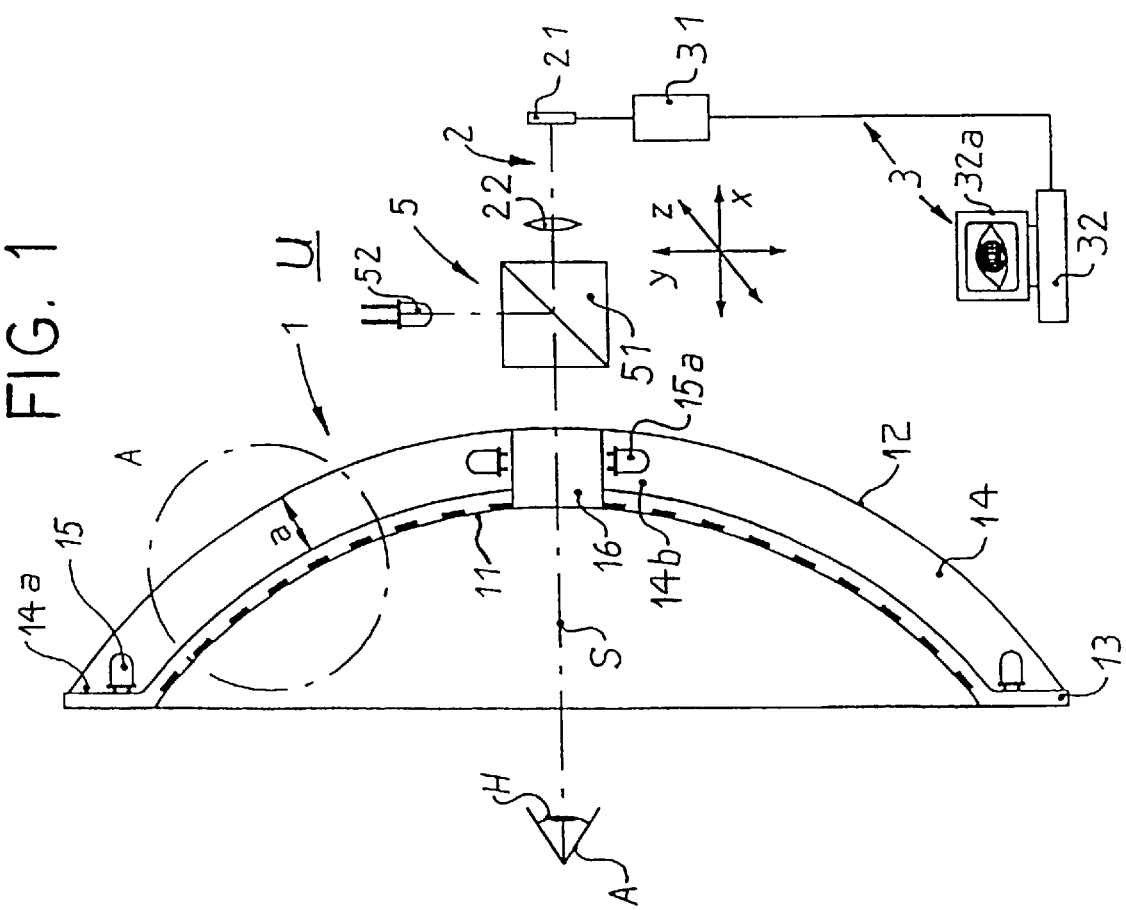

DEVICE FOR THE TOPOGRAPHICAL MEASUREMENT OF A SURFACE OF A HUMAN EYE

FIELD OF THE INVENTION

The invention relates to a device for the topographical measurement of a surface, in particular the cornea of the human eye, comprising a projector, in which a screen aperture or the like illuminated by at least one internal light source reproduces a pattern on the surface, comprising a sensory mechanism for detecting the pattern reflected from the surface, and comprising an evaluating digital unit for the patterns or images detected by the sensory mechanism.

BACKGROUND OF THE INVENTION

Systems of concentric, alternately light and dark rings are as a rule used as the pattern. They can be produced in various ways. Thus, it is, for example, possible to mount reflecting ring marks inside of a hollow spherical or paraboloidally shaped housing, on which the light from a light source provided in the optical axis is reflected, as this is, for example, already described in the Patent DE 32 33 178 C2. Such a device demands a considerable amount of industrial input: The ring marks must be constructed with extraordinary precision and must be arranged in the housing in order to produce a regular pattern. Small errors in the position of the reflecting surfaces on the ring marks result in considerable distortions of the pattern. The light source must be mounted rather exactly in the focal point of the concentrating reflector formed by the ring marks if the pattern is supposed to be evenly illuminated.

An arrangement of such a ring mark system, which arrangement instead is provided in a hollow-cone-shaped housing, is described in the Patent Application EP 0 589 857 A1. The housing is transparent throughout and is illuminated on the back side of the ring marks by an annular light source. The light source surrounds the housing coaxially on its front side with the small diameter, in the vicinity of which in addition a fixation point in the beam path can be reproduced, which is produced by means of a light diode and makes possible during the measurement of a cornea of an eye a (reproducible) at-rest position of the eye. The light source thereby demands a considerable energy supply without assuring a uniform illumination of the pattern. Small form and/or position errors of the ring marks are also in this arrangement disadvantageous for the uniformity of the pattern.

It is known from the German Offenlegungsschrift DE 43 25 494 A1 to construct the image pattern with the help of a hollow truncated-cone-shaped screen aperture, in which the annular aperture elements alternate with annular gaps. The screen aperture is illuminated by a surrounding light source and produces also a pattern of light and dark rings on the spherical surface, which is to be measured and is provided in its axis and in front of the larger front side. Such a screen aperture can be manufactured relatively easily and with precision so that the pattern is produced with a good regularity without much input and/or expense.

A pattern, which is reproduced in this manner, for example, on the cornea of an eye, can be measured with the help of a sensory mechanism; a video camera is, for example, suitable for this purpose.

The measurement results, which are evaluated by means of a suitable evaluating digital unit, are readied by the sensory mechanism and are, if desired, compared with a pattern. The measurement results are used, for example, to fit contact lenses or to guide surgical instruments during the surgical correction of curvature radii if the cornea of an eye was measured with the device.

Fluorescent lamps formed in most cases into a circular ring are used as light sources, which lamps demand much space and emit much heat during operation. Their glare is undesired during the measuring of the cornea of the eye.

A device for the topographical measurement of a surface is known from EP 0 397 962, in which the individual light spots on the surface of a hollow conical housing are produced by a plurality of light-emitting diodes, which directly and without additional illumination of a screen aperture produce a light pattern.

SUMMARY OF THE INVENTION

The basic purpose of the invention is to overcome the described deficiencies and to provide a device of the type described in detail above in such a manner that a high-performance, glare-free light source can be installed in the smallest space, which produces only little heat and which therefore does not require any structural measures for its discharge from the area of the device.

This purpose is attained according to the invention in such a manner that the internal light source is assembled of a plurality of preferably evenly distributed light-emitting diodes. Its light density can be relative so that the glare and the heat development can be kept low. The light-emitting diodes have moreover the advantage of a long life so that the device is at all times ready for operation and must only rarely receive a new light source.

A particularly evenly and uniformly illuminated pattern is obtained with the device of the invention when the screen aperture is covered on its side not facing the surface to be measured at a distance by a reflecting surface constructed on a reflector, in which furthermore the internal light source is provided in an aperture chamber formed in this manner and defined by the reflector and the screen aperture, and in which finally the screen aperture consists of a good transparent or light permeable material, in particular plexiglass, on which the nontransparent or less transparent aperture elements forming the pattern are mounted preferably in correspondingly recessed annular grooves of the screen aperture.

The light emitted from the light source is thereby multifarious and is thus reflected in such a manner that the screen aperture is evenly and uniformly illuminated, and a homogeneously illuminated pattern is produced on the surface to be measured without the necessity of particularly powerful light-emitting diodes which would typically have to be provided for this purpose. Alternatively, it is even possible to use for the internal light source light-emitting diodes, which diodes emit infrared light so that when measuring the cornea of an eye, light sensations in the eye of a patient are avoided.

The screen aperture is advantageously constructed as a hollow spherical segment or as a hollow truncated cone, in which the aperture elements are designed best as closed rings so that in this manner a pattern with the desired alternating arrangement of concentric rings differing in brightness can be comfortably produced. The rings can thereby vary in cross sections, however, the arrangement is particularly simple when those with a flat rectangular cross section are used so that annularly closed bands or belts exist, which are mounted in matching flat rectangular annular grooves worked into the inner surface of the screen aperture.

It is advantageous for an even and uniform illumination when the reflecting surface of the reflector is, in the area of the aperture chamber, at all times located at a constant distance from the screen aperture, which means that the surfaces of the screen aperture and of the reflector are similar to one another.

The aperture elements are fastened on the side of the screen aperture which does not face the aperture chamber so that it is possible also without difficulties to support these aperture elements on the side facing the aperture chamber with a reflecting layer, which thus, when the aperture elements including the reflecting layer are provided in a common annular groove of the screen aperture, are provided at the base of the annular groove. The reflecting layer reflects the light emitted from the light source into the aperture chamber so that an absorption in the aperture elements and their heating up is countered.

It is advantageous when the aperture elements are constructed like a system of concentric, spaced-apart circular rings so that also the pattern follows such an arrangement; its deformation on the surface to be measured results as a rule in circles or ellipses, which can be easily mathematically processed.

A particularly preferred embodiment of the invention includes a passage provided in the optical axis in the screen aperture. It is possible to thereby arrange, between the projector and the sensory mechanism in the beam path exiting from the passage, a beam splitter for reflecting an external light source onto the surface. It is possible in this manner to utilize, completely independent of the pattern produced with the screen aperture, a device also for the measurement of the reaction of a pupil to sudden glare, assuming the sensory mechanism can detect the movement of the pupil, which movement has been caused by the glare, and convert same into digital measurement signal sequences which can be suitably processed in the evaluating digital unit. Suitable computing programs are, however, available so that the evaluation of such a measurement is generally possible. A device has been created in this manner which goes beyond the actual purpose of the invention, which when it is used in the field eye care is at the same time able to carry out the two functions of the static measurement of the cornea of the eye and of determining a reaction of the pupils.

It is in particular advantageous when the internal light source is assembled of light-emitting diodes concentrically annularly surrounding the optical axis. Several internal light sources can be provided, for example, in such a manner that the light sources are provided on the outer edge of the screen aperture facing the surface to be measured and/or on the inner edge of the screen aperture not facing the surface to be measured, in particular adjacent the passage. A homogeneous illumination can in this manner be guaranteed with certainty.

BRIEF DESCRIPTION OF THE DRAWINGS

The invention will be discussed hereinafter in greater detail in connection with one exemplary embodiment and the drawing, in which:

FIG. 1 is a center longitudinal cross-sectional view of a first embodiment of a device of the invention, FIG. 2 shows a detail A of FIG. 1, slightly enlarged.

DETAILED DESCRIPTION

A device of the invention consists according to FIG. 1 essentially of a projector 1, a sensory mechanism 2, an evaluating digital unit 3; a mechanism for any desired movement of the projector 1 together with the sensory mechanism 2 and an optionally attached glare device 5 in the three spacial directions symbolically indicated by direction components x, y, z, which direction components are positioned orthogonally with respect to one another.

Figure 4:
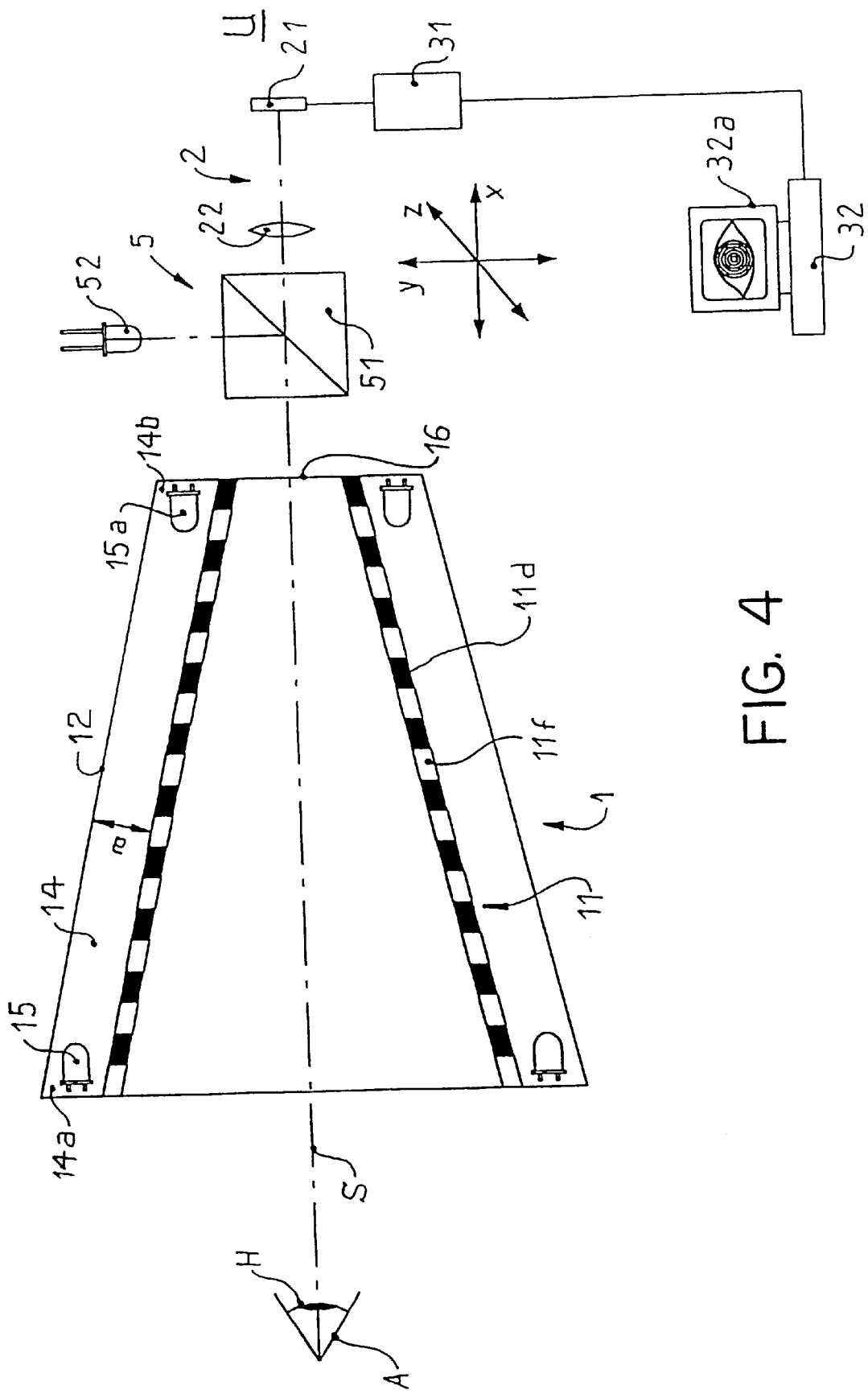
FIG. 4 shows a further embodiment of the device of the invention, all in a simplified, schematic illustration.

The projector 1 is designed as a hollow spherical segment in FIG. 1, whereas it is designed as a hollow truncated cone in FIG. 4, however, all other building and operating elements are arranged the same in both embodiments.

FIG. 1 shows that the projector 1 consists of a screen aperture 11 and a reflector 12, which are mounted in a common housing 13 only schematically indicated in the drawing in such a manner that the reflector 12 with its reflecting surface 12a is always spaced at the same distance a from the surface of the screen aperture 11 and a curved aperture chamber 14 is formed in this manner. The inner, closed surface 12a of the reflector 12 is strongly reflecting so that the aperture chamber 14 is evenly filled with light when an internal light source 15 is switched on. Its action can be increased through a further light source 15a. Both light sources 15, 15a consist of a plurality of light-emitting diodes annularly distributed in a close arrangement over the periphery of the projector 1.

Figure 3:
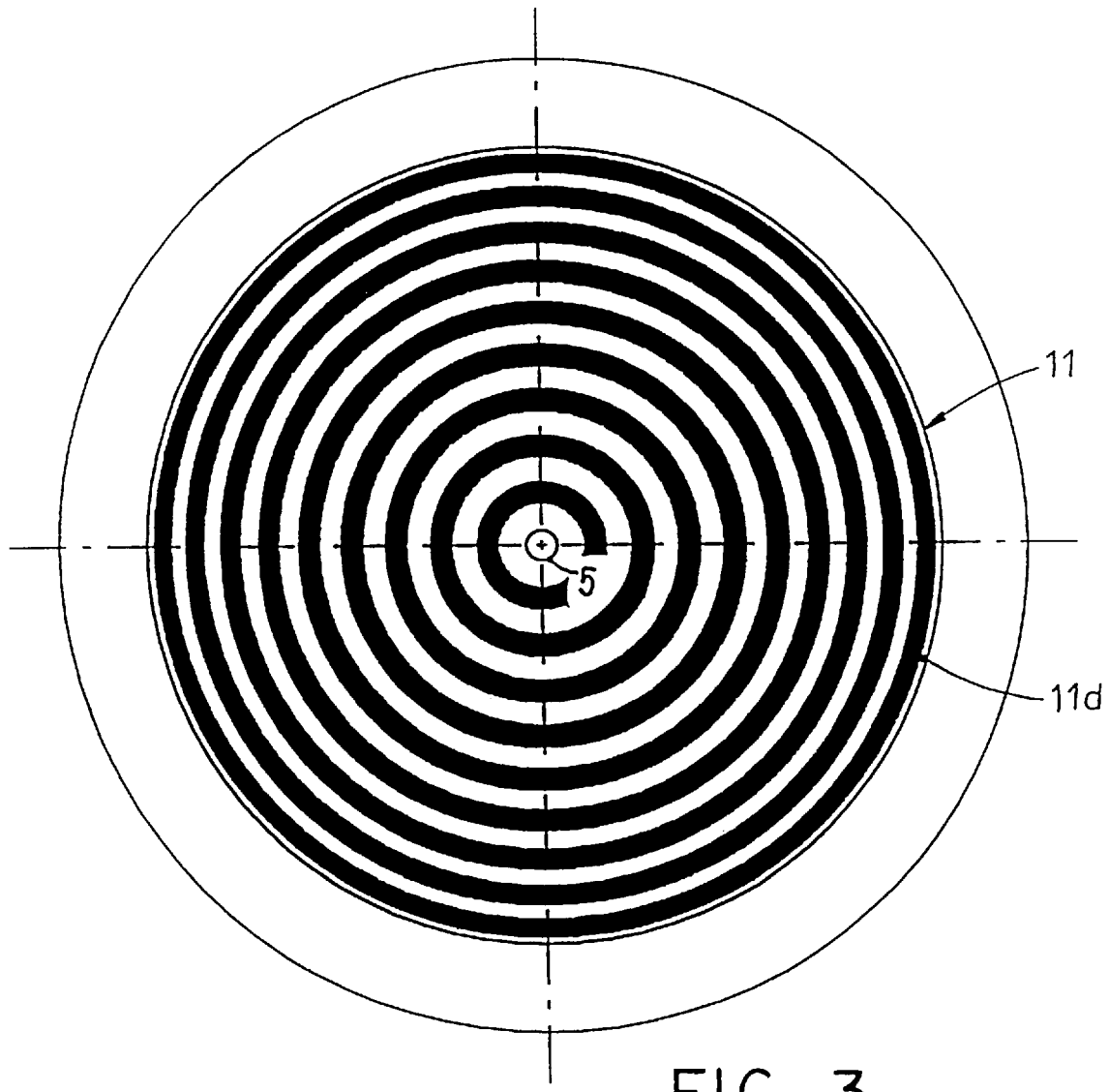
FIG. 3 is a side view of FIG. 1.

The eye A of a patient is indicated in the optical axis of the projector 1, on which eye the spherical shape of the cornea H is supposed to be measured with the device. A device for the spacial orientation of the eye A has thereby been left out of the drawing because it is known. The eye A, however, can otherwise be moved freely. The eye A sees, during the operation of the device, the projector 1 as shown in FIG. 3.

A passage 16 is provided in the axis of symmetry of the projector 1, through which passage the beam path S from the eye A is directed to the sensory mechanism 2 provided in the background U of the projector 1. The sensory mechanism consists in a simple manner of a video camera 21 with a lens 22 connected in front thereof.

The light source 15 is provided inside of the aperture chamber 14 at its outer edge 14a facing the patient, whereas the additional light source 15a, which is needed only at times and is otherwise turned off, surrounds the inner edge 14b of the aperture chamber 14 around the passage 16.

The sensory mechanism 2 is connected to an evaluating digital unit 3, with the help of which the images of the pattern, which images originate at the video camera 21 and are there already digitalized, are evaluated; the incoming image material preprocessed in a processor 31 is reproduced in a personal computer 32 on the one hand through a display 32a, and on the other hand the fed-in pattern is there made the basis for the calculation of, for example, the curvature radii of the cornea H of the eye A. The pattern consists accordingly of a ring system, which is composed originally according to FIG. 3 of concentric (circular) rings, which ring system is, for example, curved to form ellipses.

A beam splitter 51 is arranged in the beam path S between the projector 1 and the sensory mechanism 2 in the optical axis, which beam splitter, as can be recognized in FIGS. 1 and 4, consists here of a prism system. However, the beam splitter can also be assembled of partially transparent flat mirrors. An external light source 52 can be reproduced or projected in the eye A through the beam splitter 51. It is possible in this manner to produce a glare on the eye A completely independent of the remaining device so that the reaction of the eye can be detected with the help of the available sensory mechanism 2 and can also be numerically determined by the evaluating digital unit 3. A separate apparatus is therefore no longer needed for such a measurement. The beam splitter 51 and the light source 52 together form the glare device 5.

It is easy to recognize from the detail of FIG. 2 that the screen aperture 11 is assembled of several parts. Circularly shaped annular grooves 11c are recessed in a transparent corpus 11a on its surface 11b not facing or facing away from the aperture chamber 14, in which annular grooves the also circularly shaped aperture elements 11d are arranged and are supported or lined with a reflecting layer 11e, which reflecting layer 11e reflects impinging light from a light source 15, 15a into the aperture chamber 14.

FIG. 4 shows that the screen aperture 11 can also consist simply of alternately arranged annular slots 11f and aperture elements 11d.

The device operates particularly effectively when light-emitting diodes are used for the internal light sources 15, 15a, which radiate infrared light—not visible to the patient—, which infrared light, however, can be detected by a suitable sensory mechanism 2 and can be displayed on the display 32a. The eye A is then very still or is made to be very still and a sufficient glare by means of the external light source 52 is obtained already with a low light flux from the light source 52 so that the eye A is protected.

The embodiments of the invention in which an exclusive property or privilege is claimed are defined as follows:

1. A device for the topographical measurement of a surface of a human eye, comprising: a projector, in which a screen aperture illuminated by at least one internal light source reproduces a pattern on the surface; a sensory mechanism for detecting the pattern reflected from the surface; and an evaluating digital unit for the images detected by the sensory mechanism, the improvement comprising the internal light source being assembled of a plurality of evenly distributed light-emitting diodes, wherein (a) the screen aperture is enclosed on a side not facing the surface to be measured by a reflecting surface constructed on a reflector, the reflecting surface spaced a distance from the screen aperture, (b) the internal light source is provided in an aperture chamber defined by the reflector and the screen aperture, and (c) the screen aperture comprises a light permeable material on which aperture elements forming the pattern are mounted in recessed annular grooves of the screen aperture.

2. The device according to claim 1, wherein the screen aperture is constructed as a hollow spherical segment.

3. The device according to claim 1, wherein the screen aperture is constructed as a hollow truncated cone.

4. The device according to claim 1, wherein the aperture elements are constructed as closed rings with a flat rectangular cross section.

5. The device according to claim 1, wherein the distance of the reflecting surface of the reflector from the screen aperture is a constant distance.

6. The device according to claim 1, wherein the aperture elements are fastened on the side of the screen aperture which does not face the aperture chamber.

7. The device according to claim 1, wherein the aperture elements are lined with a reflecting layer on the side facing the aperture chamber.

8. The device according to claim 1, wherein the aperture elements are constructed in the form of a system of concentric, spaced-apart circular rings.

9. The device according to claim 1, wherein a passage is provided along an optical axis of the screen aperture.

10. The device according to claim 9, wherein between the projector and the sensory mechanism in a beam path exiting from the passage there is arranged a beam splitter for reflecting an external light source onto the surface.

11. The device according to claim 1, wherein the light-emitting diodes concentrically annularly surround an optical axis.

12. The device according to claim 1, wherein the topographical measurement of the surface of the human eye comprises measurement of the cornea.

13. The device according to claim 12, wherein the plurality of light emitting diodes are provided on an outer side of the screen aperture facing the surface to be measured.

14. The device according to claim 12, wherein a passage is provided along an optical axis of the screen aperture and the light-emitting diodes are provided on an inner side of the screen aperture, the inner side not facing the surface to be measured.

15. The device according to claim 1, wherein the light-emitting diodes emit infrared light.

16. In a device for the topographical measurement of a surface of a human eye, a projector comprising:

a screen aperture for producing a pattern on the eye, said screen aperture comprising aperture elements and a light permeable material having recessed annular grooves;

a reflector having a reflecting surface facing said screen aperture;

an aperture chamber defined by said reflector and said screen aperture, said reflector and said screen aperture being spaced from each other and having a distance therebetween; and at least one light source in said aperture chamber for emitting light to enable said screen aperture to produce the pattern.

17. In the device of claim 16, wherein said aperture elements of said screen aperture, said at least one light source, and said reflector produce the pattern to measure the surface of a cornea of the eye.

18. In the device of claim 16, said at least one light source comprising a plurality of light emitting diodes emitting infrared light.

\* \* \* \* \*